(12) United States Patent
Schnitzler

(10) Patent No.: US 6,579,289 B2
(45) Date of Patent: Jun. 17, 2003

(54) PROBE ELECTRODE

(75) Inventor: Uwe Schnitzler, Tübingen (DE)

(73) Assignee: Erbe Elektromedizin GmbH, Tubingen (DE)

(*) Notice: Subject to any disclaimer, the term of this patent is extended or adjusted under 35 U.S.C. 154(b) by 0 days.

(21) Appl. No.: 09/883,824

(22) Filed: Jun. 18, 2001

(65) Prior Publication Data
US 2002/0016590 A1 Feb. 7, 2002

(30) Foreign Application Priority Data
Jun. 19, 2000 (DE) .......................... 100 30 111

(51) Int. Cl.⁷ .............................. A61B 18/18
(52) U.S. Cl. .......................... 606/49; 606/46
(58) Field of Search ................. 606/48, 49, 50, 606/46, 41, 45

(56) References Cited

U.S. PATENT DOCUMENTS

| | | |
|---|---|---|
| 5,088,997 A | 2/1992 | Delahuerga et al. |
| 5,207,675 A | 5/1993 | Canady |
| 5,496,314 A * | 3/1996 | Eggers .................. 606/41 |
| 5,626,576 A * | 5/1997 | Janssen ................. 606/41 |
| 5,720,745 A * | 2/1998 | Farin et al. ............. 606/49 |

FOREIGN PATENT DOCUMENTS

DE 41 39 029 A1 6/1993

OTHER PUBLICATIONS

Technology of Argon Plasma Coagulation with Particular Regard to Endoscopic Applications; *Endoscopic Surgery and Allied Technologies*; vol. 2, No. 1, pp. 71–77.

* cited by examiner

*Primary Examiner*—Michael Peffley
*Assistant Examiner*—Aaron Roane
(74) *Attorney, Agent, or Firm*—Marshall, Gerstein & Borun

(57) ABSTRACT

A probe for the electrosurgical treatment of tissues, in particular by way of an endoscope, comprises a pipe-shaped or tubular supply device to guide a noble gas from a noble-gas source to a distal end of the supply device, and an electrode. The electrode comprises a discharge portion and an electrical lead which conducts a HF current from a HF source to the discharge portion. The discharge portion is formed as a flat structure and disposed in the supply device in such a way that the noble gas can flow over a substantial portion of its surface area so as to conduct away heat.

9 Claims, 3 Drawing Sheets

PROBE ELECTRODE

FIELD OF THE INVENTION

The present invention relates to a probe for electrosurgical treatment of tissues, in particular by way of an endoscope. Probe electrodes of this kind are used to stanch the bleeding of tissues, for example in the gastrointestinal tract in general or in the colon.

DESCRIPTION OF THE PRIOR ART

German patent DE 4139029 A1 describes a device for the coagulation of biological tissue, to be used in an endoscope with a working channel, which comprises an electrical lead to be connected to a HF voltage source in order to supply coagulation current to the tissue from the distal end of the endoscope. An ionizable gas can be passed through the working channel from a gas reservoir. Within the path along which the gas flows before emerging from the nozzle opening, there is disposed an electrode connected to the electrical lead, the purpose of which is to ionize the gas and provide the coagulation current. When the apparatus is within a specific ignition distance from the tissue to be treated, an electrical arc passes from the electrode through the ionized gas into the tissue and raises the temperature of the tissue to the level necessary to stop the bleeding. In this design the electrode has a cylindrical shape and is disposed at the inner edge just ahead of the opening of the connecting lead.

In U.S. Pat. No. 5,207,675 an apparatus is described in which the coagulation of biological tissue is achieved by means of a biocompatible, flexible tube that can be movably inserted into an endoscope. This tube conducts argon gas from a gas reservoir to the distal end of the tube. A wire running through the tube is connected to a HF voltage source from which coagulation current is supplied. This wire terminates in a tungsten tip that serves as an electrode; positioned at the distal end of the tube, it ionizes the gas that emerges there and enables a discharge to be conducted through the gas stream into the tissue. As a result of the HF energy applied through this arc, the tissue is brought to the temperature required to stop bleeding. The electrode here has the form of a wire with a tungsten tip. As alternatives to this tip, various surgical instruments such as a gripper, a scalpel or the like can be installed.

From the publication Farin G.; Grund K. E.: Technology of Argon-Plasma-Coagulation with particular regard to endoscopic application; in: Endoscopic surgery and allied technologies; Vol. 2, 1994, No. 1, pp. 71–77, it is known that the direction and extent of this arc, i.e. its overall geometric form, is determined less by the gas current than by the electrical relationships, in particular those of the tissue to be treated. Therefore in many cases in which plasma coagulation is employed, it is extremely problematic to treat precisely the places in the tissue that need to be treated, while leaving adjacent parts of the tissue unaffected. Owing to the special requirements of endoscopic treatment, these problems are exacerbated here.

In view of the circumstances outlined above, it is impossible to predict accurately the effect of such a treatment method, because of the limited precision with which the direction of the arc (also called "beam" below) can be determined. Furthermore, the extent and hence uniformity of the beam over the intended target region of the tissue to be treated is difficult to estimate, which in the end result forces the operator to position the electrode as close as possible to the target region in order to avoid missing it. But this increases the risk that the hot electrode will make contact with the tissue, with the result that the tissue will adhere to it and the source of bleeding will be torn open again.

According to the state of the art, as shown in FIG. 6, to avoid this risk appropriately shaped spacer pieces 80 made of poorly heat-conducting material, such as ceramic, have been placed onto the distal end of a tube 90. However, this also increases it the distance between a distal tip 71 of an electrode, which as indicated in FIG. 6 has the form of a helical discharge portion 70 of an electrical lead 30, and the tissue to be treated, with the disadvantages described above for the efficiency of the beam. Furthermore, the distal tip 71 fitted in the distal end of the tube 90 makes it necessary for the correspondingly shaped electrode to be centered during its insertion from the proximal end 92 of the tube 90 into the exit opening 91 of the spacer piece. Such an elaborately constructed probe is expensive and its service life is limited by the tendency of the electrodes previously employed to burn away.

The problems just described are not satisfactorily solved by any of the devices known so far.

The object of the present invention is to provide a probe for the electrosurgical treatment of tissues which can be manufactured by a simple means and which can be easily manipulated in the operation area, in particular with respect to the distance from the tissue to be treated at which the distal end must be positioned and with respect to an associated reduction of the risk of injury. At the same time, it is intended to provide a probe with an enhanced efficiency of the beam, with respect for example to ease of ignition as well as more precise aiming and greater uniformity.

SUMMARY OF THE INVENTION

According to the present invention there is provided a probe for the electrosurgical treatment of tissues comprising a tubular supply device to guide a noble gas from a noble-gas source to a distal end of the supply device; and an electrode comprising a discharge portion and an electrical lead which can conduct a HF current from a HF source to the discharge portion, the discharge portion being formed as a flat structure that is disposed in the supply device such that the noble gas can flow over a substantial portion of its surface area to conduct away heat.

As the discharge portion of the probe is constructed with a suitably large surface area, heating of the probe is avoided. The discharge portion, which is disposed at the distal end of the supply device with its flat surfaces extending in the direction of flow, is thus completely surrounded by the stream of noble gas, as a result of which heat is conducted away.

Hence, there is no longer any need for structural features designed to avoid injury caused by the hot probe electrode, such as the elaborately designed tube tip with a spacer piece, at least in the case of disposable probes. Furthermore, a special centering of the discharge portion within the exit opening of a spacer piece is no longer required, which enables this portion to be constructed more simply and cost-effectively. In addition, the dissipation of heat makes it possible to minimize the rate at which the discharge portion of the probe burns away, which increases its service life.

Because the discharge portion defines a large, flat region parallel to the direction of gas flow, turbulence in the gas flow in this region is reduced, which increases the uniformity and directional precision of the gas stream.

Preferably, the discharge portion of the probe is so constructed that it comprises at least one tip or sharp edge that faces toward the distal end.

As a result of this construction, the electromagnetic field is condensed onto the tip or sharp edge that is closest to the tissue to be treated, which increases the field strength in this region. It can thus be ensured that the beam originates from the centered tip of the discharge portion. Hence the field strength is increased and the ionization of the gas is improved, as a result of which the ignition distance between discharge portion and tissue to be treated is enlarged.

Preferably, the discharge portion comprises a lamina, with dimensions such that opposed edges of the lamina are fixedly engaged with an interior wall of the supply device surrounding the discharge portion. In this case the thin plate of which the discharge portion is composed can either be flat or, if spinning and turbulence of the gas stream are desired, it can be twisted.

This arrangement offers the advantage that the discharge portion becomes automatically centered in the supply device, which from a manufacturing point of view requires less expenditure of effort on adjustment and hence is more economical. It further ensures that the beam originates from the center of the supply device, which reduces the amount of heat transmitted to the supply device. In addition, the material for the lamina-shaped discharge portion is easy to obtain and also easy to process, e.g. by an etching method.

Preferably, the supply device, including its distal end, is made in one piece out of a plastics material. Because the spacer piece is eliminated by the design of the discharge portion described above, the supply device is made less complicated in structure and can thus be more economically manufactured.

Preferably the electrical lead comprises a wire and the discharge portion is made of sheet metal, the wire and the discharge portion being connected by spot-welding at at least one site. Connection of the wire to the lamina can be performed especially favorably by means of resistance welding, which offers additional advantages regarding manufacturing technique.

The present invention will now be described by way of example with reference to the accompanying drawings.

DESCRIPTION OF THE PREFERRED EMBODIMENTS

Figure 1:
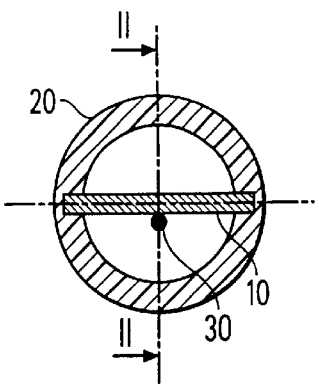
FIG. 1 is a cross sectional view of a first embodiment of a probe according to the invention, along the line I—I in FIG. 2.
Figure 2:
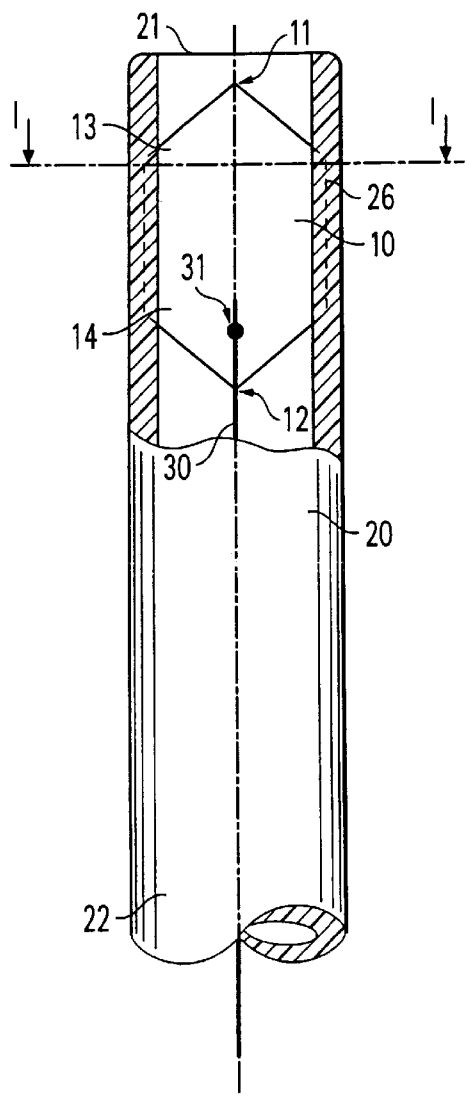
FIG. 2 is a section along the line II—II in FIG. 1.

In FIGS. 1 and 2 a first embodiment of the invention is shown, in which an electrode comprises a discharge portion 10 which is formed as a flat structure and preferably as a lamina with a sharp distal tip 11 and sharp proximal tip 12 or edge of arrow-shape at both proximal 14 and distal 13 ends. The discharge portion 10 is preferably made of sheet metal and is joined to an electrical lead 30, in the form of a wire, by way of at least one spot-welded connection 31. The discharge portion 10 is fixed centrally in a tubular supply device 20 and is dimensioned such that the edges of the lamina 26 are in fixating engagement with an inner wall of the supply device 20. Preferably, the supply device 20, including its distal end 21, is made in one piece out of a plastic material.

Figure 6:
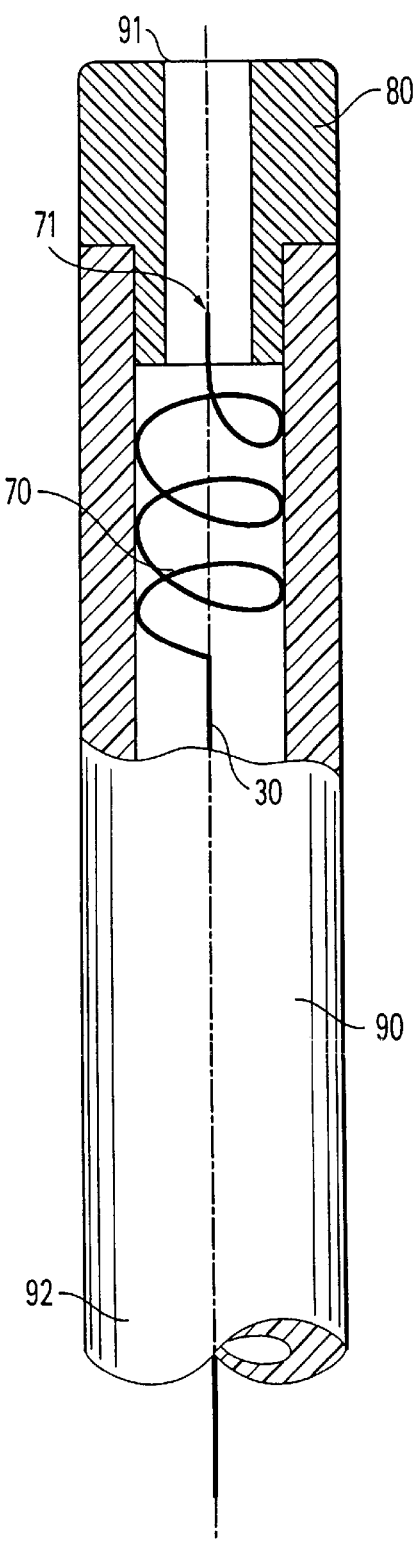
FIG. 6 is a longitudinal cross sectional view of an embodiment of a probe according to the state of the art.

The basic idea underlying this embodiment of the invention is to utilize a stream of noble gas supplied from a proximal end 22 of the supply device 20 in two ways. First, it serves as an electrical medium to transmit a current from the discharge portion 10 into the tissue to be treated, by ionization; and second, it constitutes a thermal medium to dissipate by convection the heat thus produced at the discharge portion 10. This dual function is ideally fulfilled by the configuration of the discharge portion 10. The lamina oriented parallel to the direction of flow provides a surface area large enough to give off heat adequately. Furthermore, as a result of this configuration the aerodynamic turbulence of the gas stream is reduced to a minimum. Then, by means of a centered distal tip 11, the applied HF voltage is discharged into the tissue to be treated. The thermal relationships at the discharge portion 10 now enable the thermally insulating spacer piece 80, which was required in the arrangement shown in FIG. 6, to be omitted, because the thermal stress on the conductor 20 is reduced. Altogether, this has several simultaneous positive effects.

Because the ionization of the gas as shown in FIGS. 1 and 2 is improved in comparison with the state of the art, and also as a result of the absence of the spacer piece 80, the electric field that induces discharge is enhanced by the arrangement in FIG. 2. Therefore the ignition distance between the distal tip 11 of the discharge portion 10 and the tissue is increased, and owing to the greater field strength and the decreased turbulence of the gas stream, the beam becomes more accurately directed toward the target and more uniform. Hence the operator need no longer position the probe close to the tissue to be treated, as was previously required, and therefore can more easily avoid injuries. At the same time he obtains a better overview of the operation region. The large area of the discharge portion 10 increases the service life of the probe electrode.

Figure 3:
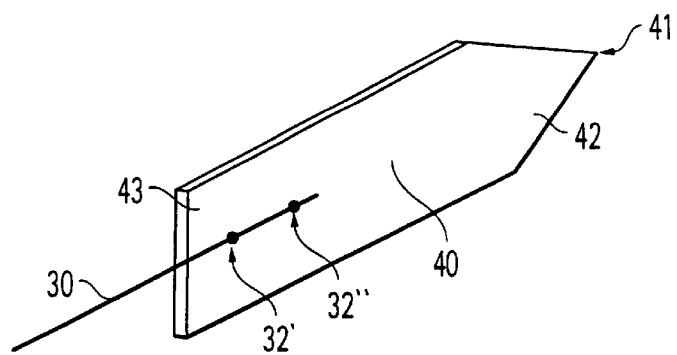
FIG. 3 is a perspective view of a discharge portion of a second embodiment of probe according to the invention.
Figure 4:
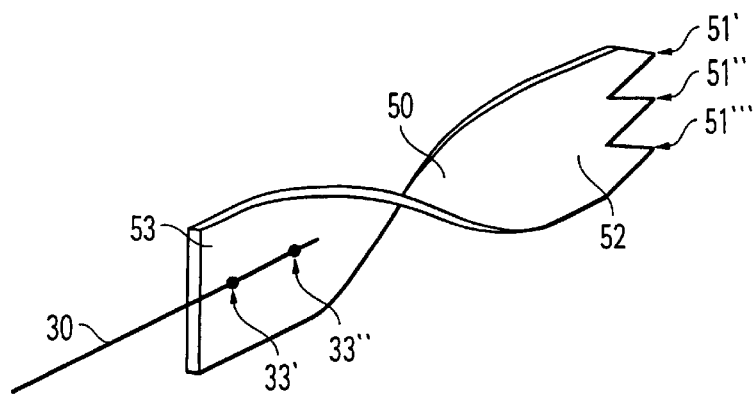
FIG. 4 is a view similar to that in FIG. 3, but showing a twisted discharge portion.
Figure 5:
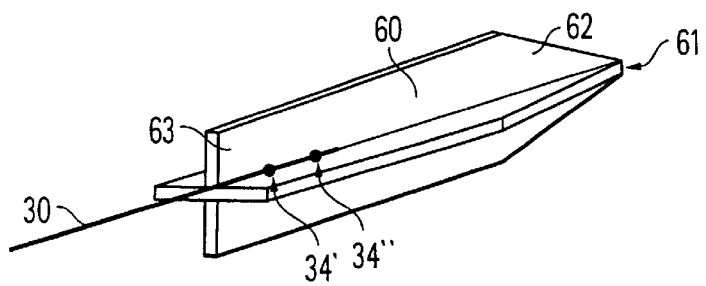
FIG. 5 is a perspective view of a discharge portion in a further embodiment of probe according to the invention.

Alternatively, the discharge portion 10 can be designed as shown in FIGS. 3 to 5, where it is identified by the numerals 40, 50 and 60 respectively. The basic idea underlying these embodiments is to achieve a special configuration of the gas stream, and hence the beam, at the point of emergence from the distal end of the supply device 20. The proximal end 14 of the discharge portion may also be made arrow-shaped, as shown in FIG. 2, in this embodiment too. Such a configuration makes it easier during manufacture to introduce the discharge portion 10, 40, 50 or 60 with the electrical lead 30 into the supply device 20 from its distal end 21.

In one embodiment, a laminar flow is generated by appropriately shaping the discharge portion 40 and 60 as shown in FIG. 3 and FIG. 5. The configuration in FIG. 3 begins with multiple spot-welds, 32' and 32", at the proximal end 43. The distal end 42 eventually comes to a sharp distal tip 41. The configuration in FIG. 5 has orthogonal side fins starting with multiple spot welds, 34' and 34", at the proximal end 63. The distal end 62 eventually comes to a sharp distal tip 61. The effective surface area has been increased to yield the advantages described extensively above.

Another possibility is to generate a stream that twists, by shaping the discharge portion 50 correspondingly as shown in FIG. 4. Note again the multiple spot welds 33' and 33". Into this swirling stream a beam with the greatest possible diameter is conducted, by way of multiple arrow-shaped tips 51', 51", 51''' provided at the distal end of the discharge portion 50. The twist allows a nonlaminar flow of gas to be generated. As a result, the electric arc passing through the width of the rotating gas stream automatically finds places in the tissue that have good electrical conductivity—that is, in particular operation wounds which are moist and hence bleeding that needs to be coagulated.

With regard to manufacturing technology, all the embodiments of the invention described here offer advantages associated with simplicity of construction and readily obtainable and processable materials. As a result, considerable advantages over known electric probes can be obtained with respect to cost. The configuration of the discharge portions 10, 40, 50 or 60 allows the gas stream or the nature of its flow (laminar or nonlaminar) to be influenced to suit specific requirements.

At this juncture it should be pointed out that the various aspects of each embodiment of the invention described can be used in all of the other embodiments, for example the multiple tips as shown in FIG. 4 can also be used in the embodiments shown in FIG. 3 and in FIG. 5.

What is claimed is:

1. A probe for the electrosurgical treatment of tissues comprising a tubular supply device having an inner surface to guide a noble gas from a noble-gas source to a distal end of the supply device; and an electrode comprising a discharge portion and an electrical lead which can conduct a HF current from a HF source to the discharge portion, the discharge portion being formed as a flat structure that is immovably fixed to and completely disposed in the supply device with opposite edges of the flat structure in contact with opposites sides of the inner surface such that, during discharge of HF-current, the noble-gas can flow over a substantial portion of its surface area to conduct away heat.

2. A probe according to claim 1, wherein the discharge portion defines at least one sharp tip or edge that points toward the distal end of the supply device.

3. A probe according to claim 1, wherein the discharge portion comprises a lamina that is dimensioned such that edges of the lamina are in fixating engagement with an inner wall of the supply device.

4. A probe according to claim 1, wherein the supply device and its distal end are integrally made from a plastics material.

5. A probe according to claim 1, wherein the electrical lead comprises a wire and the discharge portion is made of sheet metal, the wire and the discharge portion being connected by spot-welding at at least one site.

6. A probe according to claim 1, wherein the discharge portion is twisted to define a screw shape.

7. A probe according to claim 1, wherein the discharge portion defines multiple sharp tips.

8. A probe according to claim 1, wherein the flat structure substantially bisects the tubular supply device.

9. A probe according to claim 1, wherein the opposite edges of the flat structure each extends into a wall of the tubular supply device.

* * * * *